(12) United States Patent
Clark

(10) Patent No.: US 7,569,029 B2
(45) Date of Patent: Aug. 4, 2009

(54) MULTI-LUMEN CATHETER

(76) Inventor: Timothy W. I. Clark, 8516 Parkwood La., Philadelphia, PA (US) 19128

( * ) Notice: Subject to any disclaimer, the term of this patent is extended or adjusted under 35 U.S.C. 154(b) by 0 days.

(21) Appl. No.: 11/103,778

(22) Filed: Apr. 12, 2005

(65) Prior Publication Data

US 2005/0228339 A1  Oct. 13, 2005

Related U.S. Application Data

(60) Provisional application No. 60/561,430, filed on Apr. 12, 2004.

(51) Int. Cl.
*A61M 3/00* (2006.01)
(52) U.S. Cl. .................. 604/43; 604/266; 604/4.01; 604/5.01; 604/6.05; 604/6.16
(58) Field of Classification Search ............. 604/43, 604/266, 4.01–6.07, 6.16
See application file for complete search history.

(56) References Cited

U.S. PATENT DOCUMENTS

| | | | |
|---|---|---|---|
| 256,590 A | 4/1882 | Pfarre | |
| 272,651 A | 2/1883 | Coates | |
| 701,075 A | 5/1902 | McCully | |
| 2,175,726 A | 10/1939 | Gebauer | 128/349 |
| 2,819,718 A | 1/1958 | Goldman | 128/350 |
| 3,634,924 A | 1/1972 | Blake et al. | 29/447 |
| 4,072,146 A | 2/1978 | Howes | 128/2.05 |
| 4,098,275 A | 7/1978 | Consalvo | 128/214 |
| 4,134,402 A * | 1/1979 | Mahurkar | 604/44 |
| 4,180,068 A | 12/1979 | Jacobsen et al. | 128/214 |
| 4,403,983 A | 9/1983 | Edelman et al. | 604/43 |
| 4,406,656 A | 9/1983 | Hattler et al. | 604/280 |
| 4,451,252 A | 5/1984 | Martin | 604/43 |
| 4,543,087 A | 9/1985 | Sommercorn et al. | 604/43 |
| 4,568,329 A | 2/1986 | Mahurkar | 604/43 |
| 4,583,968 A | 4/1986 | Mahurkar | 604/43 |

(Continued)

FOREIGN PATENT DOCUMENTS

CA    1092927    1/1981

(Continued)

OTHER PUBLICATIONS

Dr. Sven Ivar Seldinger MD@ Congress of the Northern Assoc. of Medical Radiology at Helsinki in Jun. 1952.

(Continued)

*Primary Examiner*—Nicholas D Lucchesi
*Assistant Examiner*—Laura A Bouchelle

(57) ABSTRACT

The invention provides a catheter for placement within a vessel of a patient. The catheter comprises an elongated catheter body, a septum extending longitudinally through the interior of the catheter body from the dividing the interior of the catheter body into a first lumen and a second lumen. Each lumen has curved or angled internal walls at the distal end of the catheter that terminate at ports located on opposing sides of the catheter body. The invention also provides a method for exchanging fluids in a patient comprising the step of positioning the catheter of the present invention in communication with a fluid-containing vessel of a patient. The method is particularly well-suited for hemodialysis, plasmapheresis, and other therapies which require removal and return of blood from a patient.

23 Claims, 3 Drawing Sheets

U.S. PATENT DOCUMENTS

| | | | |
|---|---|---|---|
| 4,619,643 A | 10/1986 | Bai | 604/43 |
| 4,692,141 A | 9/1987 | Mahurkar | 604/43 |
| 5,221,255 A | 6/1993 | Mahurkar et al. | 604/43 |
| 5,348,536 A * | 9/1994 | Young et al. | 604/43 |
| 5,378,230 A * | 1/1995 | Mahurkar | 604/43 |
| 5,380,276 A | 1/1995 | Miller et al. | 604/28 |
| 5,395,316 A | 3/1995 | Martin | 604/43 |
| 5,403,291 A | 4/1995 | Abrahamson | 604/280 |
| 5,405,341 A | 4/1995 | Martin | 604/284 |
| 5,571,093 A | 11/1996 | Cruz et al. | 604/270 |
| 6,001,079 A | 12/1999 | Pourchez | 604/43 |
| 6,190,349 B1 * | 2/2001 | Ash et al. | 604/43 |
| 6,409,700 B1 * | 6/2002 | Siegel et al. | 604/43 |
| 6,461,321 B1 * | 10/2002 | Quinn | 604/43 |
| 6,719,749 B1 | 4/2004 | Schweikert et al. | 604/544 |
| 6,758,836 B2 | 7/2004 | Zawacki | 604/284 |
| 6,786,884 B1 | 9/2004 | DeCant, Jr. et al. | 604/43 |
| 7,141,035 B2 * | 11/2006 | Haggstrom | 604/43 |
| 2003/0144623 A1 * | 7/2003 | Heath et al. | 604/4.01 |
| 2004/0167463 A1 * | 8/2004 | Zawacki et al. | 604/43 |
| 2005/0228339 A1 | 10/2005 | Clark | 604/43 |

FOREIGN PATENT DOCUMENTS

CA      1150122      7/1983

OTHER PUBLICATIONS

Dr. Shaldon—1961 edition of The Lancet at pp. 857-859.
Dr. Uldall—Dialysis & Transplantation, vol. 8, No. 10 in Oct. 1979.

* cited by examiner

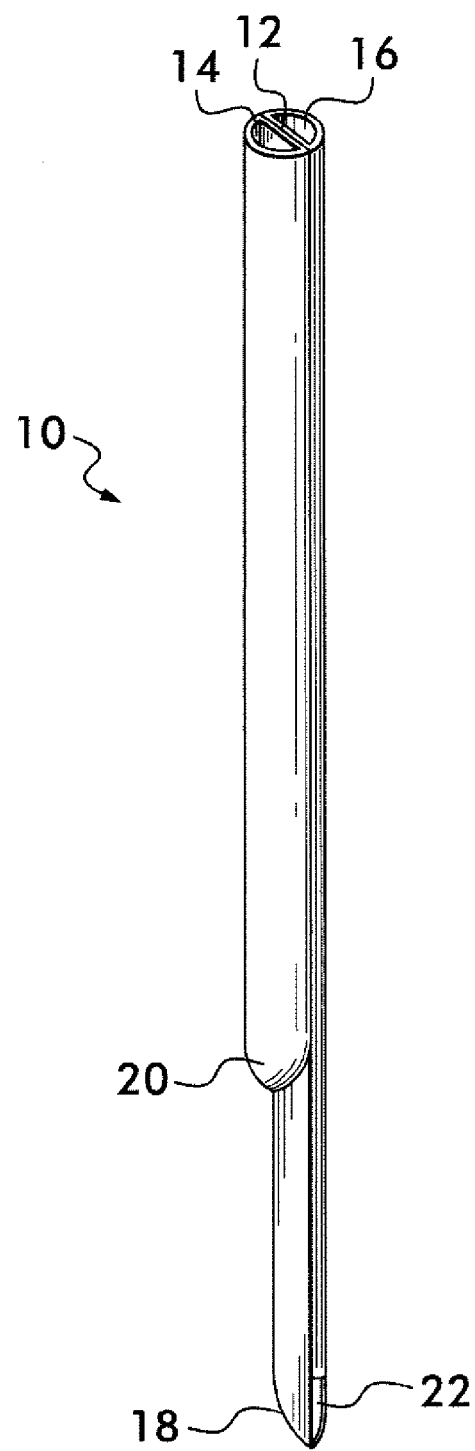

MULTI-LUMEN CATHETER

CROSS-REFERENCE TO RELATED APPLICATION

This application claims the benefit of U.S. Provisional Application No. 60/561,430, filed on Apr. 12, 2004, which is incorporated herein in its entirety.

FIELD OF THE INVENTION

The present invention relates to a multi-lumen catheter, and more specifically, a dual-lumen catheter with entry and exit ports having curved or angled walls to direct the flow of fluids therethrough.

BACKGROUND OF THE INVENTION

Dual-lumen catheters have been available for many years for a variety of medical purposes. It is only in recent years, however, that such catheters have been developed for use in hemodialysis and other treatments which involve the removal and replacement of blood. The general form of dual-lumen catheters goes back to as early as 1882 when Pfarre patented such a catheter in the United States under Ser. No. 256,590. This patent teaches a flexible dual-lumen catheter which is used primarily for cleaning and drainage of, for example, the bladder, rectum, stomach and ear. In this type of catherization, the catheter is introduced into an existing body orifice without the use of any puncturing needle or guide wire.

More recently, a catheter was developed and patented by Blake et al. under U.S. Pat. No. 3,634,924. This patent teaches a double lumen cardiac balloon catheter which is introduced into a large vein and the balloon is inflated to control the flow in the vein. The catheter can be placed by using the balloon as a "sail" to move with the blood from an ante-cubital or other peripheral vein through for example, the right heart chambers into the smaller radicals of the pulmonary artery where the catheter takes up its intended function. This patent teaches the use of two lumina in a single body and explains how to make a tip for a dual-lumen structure of the type which has become common for a variety of purposes including hemodialysis. The structure uses a plug to seal the end of one lumen and a wire which retains the shape of the other lumen during formation of the tip in a heated die.

Further patents which teach dual-lumen or multiple lumen catheters for general use include the following: U.S. Pat. Nos. 701,075; 2,175,726; 2,819,718; 4,072,146; 4,098,275; 4,134,402; 4,180,068; 4,406,656; 4,451,252; 5,221,255; 5,380,276; 5,395,316; 5,403,291; 5,405,341; 6,001,079; 6,190,349; 6,719,749; 6,758,836; and 6,786,884, the disclosures of each of which are incorporated herein in their entirety.

Vascular catheter access techniques have been known to the medical profession for many years and, in fact, can be traced back to the 17th century. However, it was only with the introduction of the Seldinger technique in the early 1950s that a new approach could be used to improve vascular access. This technique was taught in an article published by Dr. Sven Ivar Seldinger resulting from a presentation made at the Congress of the Northern Association of Medical Radiology at Helsinki in June of 1952. The technique essentially involves the use of a hollow needle to make an initial puncture, and a wire is then entered through the needle and positioned in the vessel. The needle is withdrawn and the catheter is entered percutaneously over the wire which is itself later withdrawn. With this technique it became possible to make less traumatic vascular access and this has now become the accepted method of performing access in numerous medical techniques. One of these techniques which been the subject of much research and development is hemodialysis.

Hemodialysis can be defined as the temporary removal of blood from a patient for the purpose of extracting or separating toxins therefrom and the return of the cleansed blood to the same patient. Hemodialysis is indicated in patients where renal impairment or failure exists, that is, in cases where the blood is not being properly or sufficiently cleansed, particularly to remove waste materials and water, by the kidneys.

In the case of chronic renal impairment or failure, hemodialysis has to be carried out on a repetitive basis. For example, in end-stage kidney disease where transplantation of kidneys is not possible or for medical reasons is contra-indicated, the patient may have to be dialyzed about 100 to 150 times per year. This can result in several thousand accesses to the blood stream to enable hemodialysis to be performed over the remaining life of the patient.

Towards the end of 1960, Dr. Stanley Shaldon and colleagues developed, in the Royal Free Hospital in London, England, a technique for hemodialysis by percutaneous catheterization of deep blood vessels, specifically the femoral artery and vein. The technique was described in an article published by Dr. Shaldon and his associates in the Oct. 14, 1961 edition of The Lancet at Pages 857 to 859. Dr. Shaldon and his associates developed single lumen catheters having tapered tips for entry over a Seldinger wire to be used in hemodialysis. Subsequently, Dr. Shaldon and his colleagues began to insert single lumen inlet and outlet catheters in the femoral vein and this was reported in the British Medical Journal of Jun. 19, 1963. The purpose of providing both inlet and outlet catheters in the femoral vein was to explore the possibility of a "self-service" approach to dialysis. Dr. Shaldon was subsequently successful in doing this and patients were able to operate reasonably normally while carrying implanted catheters which could be connected to hemodialysis equipment periodically.

An advantage of dual-lumen catheters in hemodialysis is that only one vein access need be affected to establish continued dialysis of the blood. One lumen serves as the conduit for blood flowing from the patient to the dialysis unit and the other lumen serves as a conduit for treated blood returning from the dialysis unit to the patient. This contrasts with prior systems where either two insertions were necessary to place two separate catheters as was done by Dr. Shaldon, or a single cathether was used with a complicated dialysis machine which alternately removed blood and returned cleansed blood.

The success of Dr. Shaldon in placing catheters which will remain in place for periodic hemodialysis caused further work to be done with different sites. Dr. Shaldon used the femoral vein, and in about 1977 Dr. P. R. Uldall, in Toronto Western Hospital, Canada, began clinical testing of a subclavian catheter that would remain in place between dialysis treatments. An article describing this was published by Dr. Uldall and others in Dialysis and Transplantation, Volume 8, No. 10, in October 1979. Subsequently Dr. Uldall began experimenting with a coaxial dual-lumen catheter for subclavian insertion and this resulted in Canadian Patent No. 1,092,927 which issued on Jan. 6, 1981. Although this particular form of catheter has not achieved significant success in the marketplace, it was the forerunner of dual-lumen catheters implanted in the subclavian vein for periodic hemodialysis.

The next significant step in the development of a dual-lumen catheter for hemodialysis is Canadian Patent No. 1,150,122 to Martin. A subsequent development is shown in U.S. Pat. No. 4,451,252 also to Martin. This catheter utilizes the well-known dual-lumen configuration in which the lumina are arranged side-by-side separated by a diametric septum. The structure shown in this patent provides for a tip making it possible to enter a Seldinger wire through one of the lumina and to use this wire as a guide for inserting the catheter percutaneously. This type of structure is shown in a European Patent Application to Edelman published under No. 0 079 719, and in U.S. Pat. Nos. 4,619,643; 4,583,968; 4,568,329; 4,543,087; 4,692,141; 4,568,329, and U.S. Des. Pat. No. 272, 651, the disclosures of each of which are incorporated herein in their entirety.

In order to insert a catheter over a guide wire using the Seldinger technique, or indeed any similar technique, the tip of the catheter must possess sufficient rigidity so that it does not concertina as it contacts the skin because this would enlarge the skin puncture as the catheter is being entered over the wire. To some extent this is at odds with the desirable material qualities of the main body of catheter which should be soft and flexible for patient comfort. In an effort to solve this problem, a variety of tips have been formed within the limitations of using a single extrusion from which the body and tip are formed. The result is that the tips have in general been made by using some of the excess material found in the shorter intake lumen. This has led to other problems such as very stiff tips which are unsuitable for prolonged placement in a vein; voids which can accumulate stagnant blood; and short stubby tips which are less desirable for insertion than longer more gradual tips. Also, because there is not always sufficient material to form the tip, plugs have been added with a varying degree of success because if the plug is not placed accurately the resulting structure may have unacceptable spaces where blood can stagnate.

It must also be recognized that the degree of rigidity in the tip becomes more important if the catheter is to reside in the patient for prolonged periods, as is becoming more common in many treatments, notably hemodialysis. This is because although ideally the catheter lies in the middle of the vein, in practice it will often bear against the vessel wall. In such circumstances it is possible that a stiff tip could damage or even embed itself in the vessel wall when left in place for extended periods.

Hemodialysis, as practiced today, normally employs one of two types of catheters to remove blood from the patient for processing and return processed blood to the patient. Most commonly, a dual-lumen catheter is used, each lumen having either a generally cylindrical or semi-cylindrical configuration. Alternatively, two separate tubes, each usually having a full cylindrical configuration, are used separately to remove blood for dialysis and return the processed blood.

Flow rates possible with conventional dual-lumen catheters are usually lower than those achievable where separate tubes are used to remove blood from a vein for dialysis and then return processed blood back to the vein. Thus, the use of two tubes has become more and more popular as the capacity (maximum flow rate) of hemodialysis membranes has increased.

Hemodialysis membranes are now able to process blood at over 500 ml of flow per minute. Even higher processing rates are foreseeable. However, problems occur with both the line introducing purified blood back into the vein and the line removing blood for purification at flow rates above 300 ml per minute. A high flow rate from the venous line may cause whipping or "firehosing" of the tip in the vein with consequent damage to the vein lining. A corresponding high flow rate into the arterial line may cause the port to be sucked into the vein wall, resulting in occlusion.

The rate of flow through a catheter lumen, whether it be in a single lumen or a dual-lumen catheter, is controlled by a number of factors including the smoothness of the wall surface, the internal diameter or cross-sectional area of the tube lumen, and the length of the tube lumen. The most important factor is the cross-sectional area of the tube lumen. The force or speed of the fluid flow in a tube lumen for a given cross-sectional area is controlled by the external pumping force. This is a positive pressure pushing processed blood through the venous lumen and a negative (suction) pressure pulling unprocessed blood through the arterial lumen.

Problems encountered in providing for a high flow rate through a catheter are magnified in a dual-lumen catheter construction. Because each of the lumina in a dual-lumen catheter normally has a D-shape, it has been assumed that flow rates are limited. Furthermore, such dual-lumen catheters are, to a great extent, catheters with a main port which opens at the end of a lumen substantially on the axis of the lumen. Thus, firehosing frequently results. Firehosing may damage the vein wall, triggering the build-up of fibrin on the catheter tip. Fibrin build-up may further result in port occlusion.

There are dual lumen-catheters which utilize side ports for both outflow and inflow. An example is the catheter disclosed in U.S. Pat. No. 5,571,093 to Cruz et al. However, such catheters have not been entirely successful in solving problems related to hemodialysis with dual lumen catheters, e.g., high incidences of catheter port occlusion as well as some degree of fire-hosing. Further, the abrupt change in direction of the flow of blood from the vein into the catheter can result in trauma and damage to red blood cells, especially at higher flow rates.

SUMMARY OF THE INVENTION

An object of the present invention is to provide an improved multi-lumen catheter for use in hemodialysis, plasmapheresis, and other therapies which require removal of blood from one lumen of the catheter and return of treated blood through the other lumen.

Another object is to provide a multi-lumen catheter which is capable of accommodating high flow rates.

Yet another object is to provide a more efficient multi-lumen catheter for use in hemodialysis, plasmapheresis, and other therapies which require removal of blood from one lumen of the catheter and return of treated blood through the other lumen.

Still another object is to provide a multi-lumen catheter which permits high flow rates while reducing trauma to vessel walls and red cell damage.

Yet another object of the present invention is a multi-lumen catheter having a tip configuration which minimizes recirculation by maximizing the control and direction of blood flow into and out from the lumen ports.

The foregoing and other objects are realized in accord with the present invention by providing an apparatus which comprises an elongated catheter body for placement within a vessel, a septum that runs longitudinally through the interior of the catheter body so as to divide the interior of the catheter body into a first lumen and a second lumen each having a distal end having curved or angled internal walls that terminate at ports located on opposing sides of the catheter body. The curved or angled internal walls at the distal end of the lumina provide for a transition zone in which the flow of blood into and out from the catheter travels a path that gradually changes the direction of the flow of fluids between the direction of flow in the lumen and the direction of flow in the vessel.

In one embodiment, the change in direction of the flow pattern into and out of the catheter body is substantially helical. In other embodiments, the direction of the flow pattern into and out of the catheter body is curved, and in still other embodiments the direction of the flow pattern into and out of the catheter body is angled. In this manner, the flow patterns of these embodiments provide for more efficient exchange of blood by creating an alternate pattern of blood dynamics through the catheter lumina and the vessel.

In another embodiment, the ports of the lumina are longitudinally spaced. In this manner the withdrawal of blood to be treated and the return of treated blood are further separated so as to advantageously minimize the recirculation of treated blood with untreated blood. The length of separation may vary according with specific application, and is preferably from about 2 to about 3 centimeters. Preferably, the lumen port associated with the withdrawal of blood from the patient is "upstream" of the lumen port associated with the return of treated blood.

In another aspect of the present invention, there is provided a method for exchanging fluids in a patient comprising the step of positioning a catheter of the present invention in communication with a fluid-containing vessel of a patient.

These and other features of the invention will be more fully understood by reference to the following drawings and the detailed description set forth below.

BRIEF DESCRIPTION OF THE DRAWINGS

FIG. 5 is a third perspective view of the dual-lumen catheter of FIG. 3.

DETAILED DESCRIPTION

Figures 1, 2:
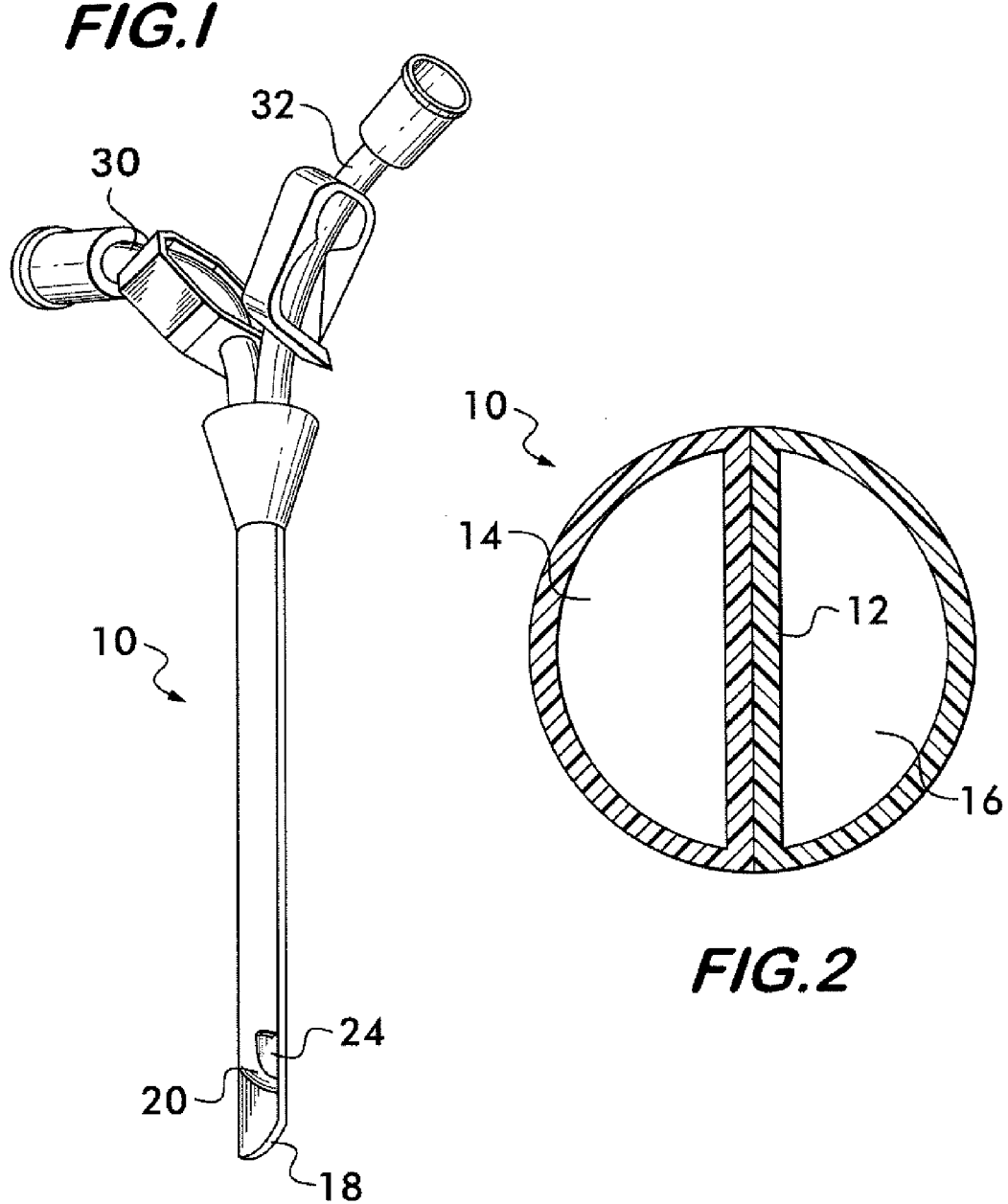
FIG. 1 is a perspective view of a dual-lumen catheter of the present invention attached to inflow and outflow tubing.
FIG. 2 is a cross-sectional view of a dual lumen catheter of FIG. 1
Figure 3:
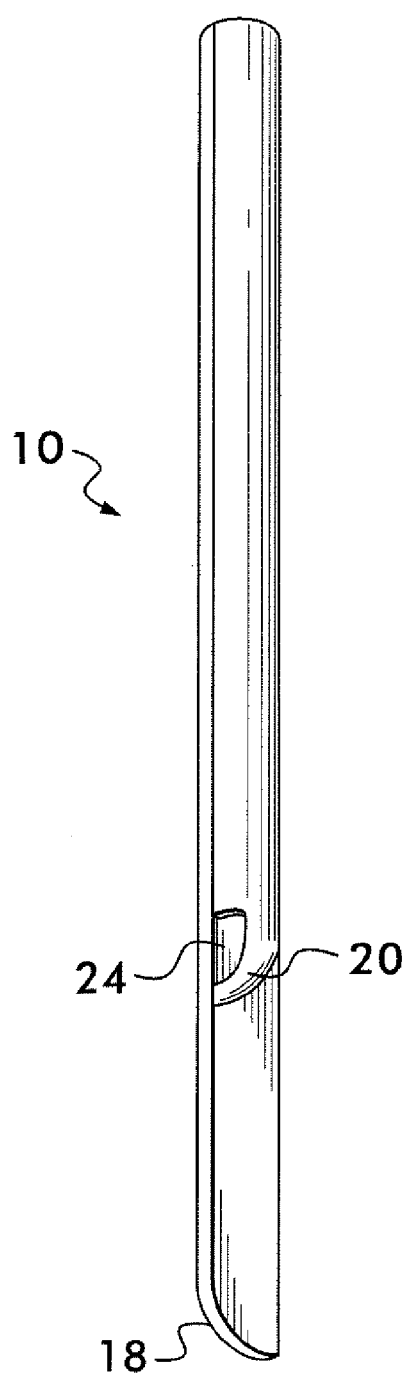
FIG. 3 is a perspective view of a dual-lumen catheter of the present invention shown apart from inflow and outflow tubing.
Figure 4:
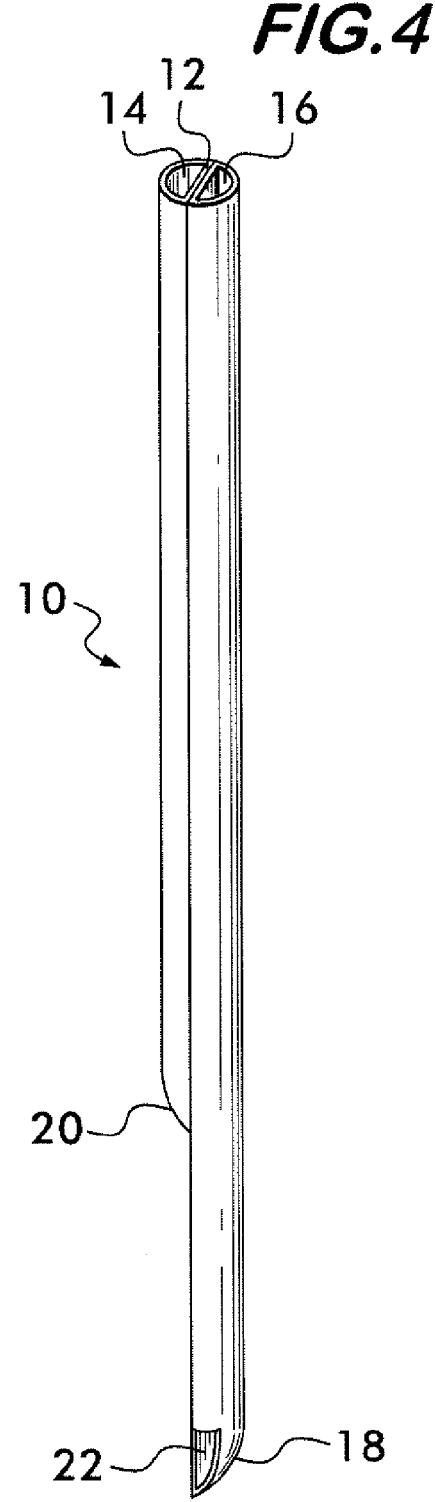
FIG. 4 is another perspective view of the dual-lumen catheter of FIG. 3.

In accordance with the apparatus of the present invention, there is provided a catheter body that is adapted for insertion into a vessel of a patient such as, for example, a vein. The catheter body comprises an external wall and a septum extending longitudinally along the internal length of the catheter body to define two substantially parallel lumina each having an internal wall and a port located at the side of the distal end thereof.

At the distal end of each lumen, at least a portion of the internal walls of the lumina are curved or angled to define a transition zone terminating at the port. So configured, the transition zone permits the flow of fluids traveling the length of the lumen to be gradually deflected from the longitudinal direction of the lumen to the transverse direction of the side-facing port at the distal end thereof.

For fluids entering the side-facing port of the lumen, the transition zone permits the flow to be gradually deflected from the direction of travel through the vessel through the lateral direction of entry to the longitudinal direction of travel in the lumen. In this fashion, the transition zone provides a gradual change in the direction of flow into and out of the lumina. This smoother and more physiologic change of direction of the fluids traveling through the lumina decreases firehosing of the catheter tip during high rates of fluid exchange, reduces stresses experienced by the fluid, and permits a more efficient and higher rate of flow into and out from the catheter. In the context of hemodialysis, plasmapheresis, and other therapies which require the transport of blood, decrease in stress provided by the transition zones at the distal end of the lumina decreases the incidence of hemolysis and trauma to the vessel lining.

In one embodiment, a first lumen of the catheter terminates in a first bolus cavity, which is formed into one side of a bolus tip at a position between the interfacing section of the lumen and a nose section of the bolus tip. The nose section of the terminal portion of the first lumen may be formed through an injection molding process to create a helical shape of the nose section and first bolus cavity so that fluids such as blood traveling through the lumen have a smooth transition of its direction of flow as it enters the first lumen. The second lumen of the catheter terminates in a second bolus cavity oriented 180 degrees from the first bolus cavity, and possesses a nose section which has a similar injection molded-configuration as the nose tip of the first lumen. The nose sections of the first and second lumina direct blood flow in directions opposite to each other thereby reducing the admixture of treated blood with non-treated blood. Preferably, the second lumen in this embodiment extends beyond the first lumen by about 2 to about 3 centimeters so that the nose section of the terminal portion of the second lumen is longitudinally spaced from the nose section of the terminal portion of the first lumen.

In another embodiment, the terminations of the first and second lumina within the nose section are partly recessed, to enable the overhanging aspect of the nose section to serve as a barrier with the vessel wall. This design is intended to reduce the phenomenon of partial or total occlusion of the lumina of the catheter.

In yet another embodiment, an additional lumen is provided within the catheter body to allow introduction of a guide wire. The guide wire inserted into this additional lumen and used to assist in the introduction and proper placement of the catheter tip into a vessel of a patient.

In still another embodiment, the first and second lumina may be split apart along the distal portion of the septum by, for example, a splittable membrane in the septum. In this manner, the lumina may be partially longitudinally separated from each other.

As used herein, reference to curvature or angularity with regard to the internal walls of the lumina includes a wide range of configurations in which at least a portion of the internal walls of the lumen at the distal ends thereof undergoes a transition in direction from the longitudinal direction of the lumen to a direction angled from such longitudinal direction. In this fashion, fluids traveling in either direction through the lumen will bear against the curved or angled wall in the transition zone in changing direction from or to a longitudinal orientation.

This change in the direction if the internal wall of the lumen in the transition zone may be constant or may vary along some or all of the transition zone, and may extend along two dimensions in which the flow path changes direction substantially within a single plane, or through three dimensions. Preferably, the curvature or angularity of the internal walls of the lumina extends in three dimensions and is substantially helical. As used herein, helical patterns includes patterns that are regular and irregular and with constant or varying diameters along their length. So configured, the movement of fluids through the transition zone imparts a helical flow pattern to such fluids. This helical flow pattern reduces the incidence of in-plane recirculation. In the context of hemodialysis, plasmapheresis, and other therapies which require the transport of blood, this helical flow pattern reduces the incidence of treated blood that is delivered to the patient through the catheter to re-enter the catheter at the intake port. The reduction of this type of recirculation allows for more efficient blood exchange and, consequently, reduced treatment time.

The cross-sectional area and geometry of the lumina may be similar to or different from each other. Preferably, the cross-sectional area of each lumen is similarly sized in order to accommodate similar flow volumes and rates into and out from the catheter. In preferred from, the cross-sectional area of each lumen is from about 3.5 mm to about 5 mm, and more preferably from about 4.5 mm to about 5 mm. The cross-section geometry of the lumina may assume a variety of shapes including circular, semi-circular (D-shaped), elliptical, semi-elliptical, teardrop-shaped, or curved teardrop-shaped resembling a yin-yang symbol.

The ports provided in the side walls of the distal ends of the lumina may accommodate a range of sizes and shapes including circular, semi-circular (D-shaped), elliptical, semi-elliptical, teardrop-shaped. Preferably, the ports are semi-elliptical and are from about 3 to about 6 mm in maximal diameter. The terminating cavities of the first and second channels have a greater surface area than prior designs such us that shown in U.S. Pat. No. 4,808,155 by Mahurkar. This results in more efficient exchange of fluids and blood.

The catheter of the present invention may be constructed from materials that are commonly used for multi-lumen catheters such as silicone or polyurethanes including polyurethanes sold under the trademark Carbothane® by Carboline Company of St. Louis, Mo.

In another aspect of the present invention, there is provided a method for exchanging fluids in a patient comprising the step of positioning a catheter of the present invention in communication with a fluid-containing vessel of a patient. In preferred embodiments, the exchanged fluid comprises blood and the fluid-containing vessel of the patient is a vein. The method of the present invention is particularly well-suited to the performance of hemodialysis, plasmapheresis, and other therapies which require removal and return of blood from a patient. The method of the present invention may further comprise the steps of ultrafiltration and/or venous sampling.

Turning now to the embodiment that is shown in the drawings and referring to FIGS. 1-5, there is shown a catheter 10 having a septum 12 bisecting the interior of catheter 10 to form two lumina 14 and 16. At the distal end of catheter 10, the lumina 14 and 16 have with curved walls 18 and 20 which terminate at ports 22 and 24 disposed on opposite sides of catheter 10. As shown in FIG. 2, the cross-section shape of lumina 14 and 16 are semicircular. In the catheter shown in FIGS. 1 and 3-5, lumen 16 extends beyond the end of lumen 14 so as to further separate the intake port 24 from outflow port 22. In operation, fluid, such as blood, enters intake port 24, changes direction as the flow of fluid passes curved wall 20 through lumen 14 to tube 32 which conveys the fluid for treatment to a device such as a dialysis machine (not shown). After treatment, the treated fluid is returned to a patient through tube 30 to lumen 16. At the end of lumen 16, the fluid is deflected by curved wall 18 and out port 22 into the vessel of the patient.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention.

I claim:

1. A catheter for placement within a vessel of a patient comprising an elongated catheter body having a proximal end and a distal end, a septum extending longitudinally through the interior of the catheter body from the proximal end to the distal end thereof dividing the interior of the catheter body into a first lumen and a second lumen each having a distal end, and internal walls at the distal ends of the lumina, wherein said internal walls define a substantially helical transition zone which gradually deflects fluids helically, in three dimensions, and said walls terminate at side facing ports located on opposing sides of the catheter body.

2. The catheter of claim 1 wherein the distal end of the first lumen extends beyond the distal end of the second lumen.

3. The catheter of claim 2 wherein the first lumen is a return lumen and the second lumen is an intake lumen.

4. The catheter of claim 2 wherein the distal end of the first lumen extends from about 2 to about 3 centimeters beyond the distal end of the second lumen.

5. The catheter of claim 1 further comprising a third lumen adapted to receive a guide wire.

6. The catheter of claim 1 wherein the first and second lumina are separated at the distal end of the catheter.

7. A catheter for placement within a vessel of a patient comprising an elongated catheter body having opposing sides and a distal end, a first lumen terminating at the distal end of the catheter body in a first bolus cavity having a helically-shaped first nose section formed on a first side of the catheter which gradually deflects fluids helically, in three dimensions, terminating at a first side-facing port disposed on the said first side of the catheter, and a second lumen terminating at the distal end of the catheter body in a second bolus cavity having a helically-shaped second nose section formed on the opposing side of the catheter for the gradual deflection of fluid helically, in three dimensions, said wall terminating at a second side-facing port disposed on the said opposing side of the catheter.

8. The catheter of claim 7 wherein the catheter comprises a silicone or polyurethane.

9. The catheter of claim 7 wherein the nose sections of the first and second lumina direct the flow of fluid in opposing directions.

10. The catheter of claim 7 wherein the distal end of the first lumen extends beyond the distal end of the second lumen.

11. The catheter of claim 7 wherein the first lumen is a return lumen and the second lumen is an intake lumen.

12. The catheter of claim 7 wherein the distal end of the first lumen extends from about 2 to about 3 centimeters beyond the distal end of the second lumen.

13. The catheter of claim 7 wherein the first and second lumina within the nose sections are partly recessed.

14. The catheter of claim 7 further comprising a third lumen adapted to receive a guide wire.

15. The catheter of claim 7 wherein the first and second lumina are separated at the distal end of the catheter.

16. A method for exchanging fluid in a patient comprising the step of positioning the catheter of claim 1 in communication with a fluid-containing vessel of a patient.

17. The method of claim 16 wherein the exchanged fluid comprises blood and the fluid-containing vessel of the patient is a vein.

18. The method of claim 16 further comprising the step of ultrafiltration.

19. The method of claim 16 further comprising the step of venous sampling.

20. A method for exchanging fluid in a patient comprising the step of positioning the catheter of claim 7 in communication with a fluid-containing vessel of a patient.

21. The method of claim 20 wherein the exchanged fluid comprises blood and the fluid-containing vessel of the patient is a vein.

22. The method of claim 21 further comprising the step of ultrafiltration.

23. The method of claim 22 farther comprising the step of venous sampling.

* * * * *